United States Patent [19]

Pasqua et al.

[11] Patent Number: 5,013,648
[45] Date of Patent: May 7, 1991

[54] ENZYMATIC DETECTION OF MONOVALENT ANIONS

[75] Inventors: John Pasqua, West Deptford; Wai T. Law, Sewell, both of N.J.

[73] Assignee: EM Diagnostic Systems, Inc., Gibbstown, N.J.

[21] Appl. No.: 242,676

[22] Filed: Sep. 9, 1988

[51] Int. Cl.$^5$ .......................... C12Q 1/26; C12Q 1/00
[52] U.S. Cl. ............................................ 435/25; 435/4; 435/26; 435/174; 435/183; 435/805; 435/810; 435/187
[58] Field of Search .................. 435/4, 25, 174, 26, 435/184, 810, 183, 187

[56] References Cited

U.S. PATENT DOCUMENTS

| | | | |
|---|---|---|---|
| 4,416,983 | 11/1983 | Röder et al. | 435/25 |
| 4,581,336 | 4/1986 | Malloy | 435/180 |
| 4,610,693 | 9/1986 | Matsui | 435/25 |
| 4,622,296 | 11/1986 | Yamanishi | 435/184 |
| 4,782,017 | 11/1988 | Frickey et al. | 435/21 |

FOREIGN PATENT DOCUMENTS 0227073  7/1987  European Pat. Off. ............... 435/4

OTHER PUBLICATIONS

White-Stevens, R. H. et al., J. Biol. Chem., vol. 247, No. 8, pp. 2358-2370 (1972).
Effects of plt and Sulfhydryl Reagents or 4 Fumaryl Acetoacetate Fumaryl Hydrolase EL-3.7.1.2., Nagainis et al., Biochim. Bio. Phys. Acta 657(1), 1981, pp. 203-211.
"Inhibition of p-Hydroxylase by Anions: Possible Existence of Two Anion-Binding Sites in the Site for Reduced Nicotinamide Adenine Dinucleotide Phosphate", Shoun et al., J. Biochem. (Tokyo), 1983, 93(1), pp. 169-176.

*Primary Examiner*—Esther L. Kepplinger
*Assistant Examiner*—Toni R. Scheiner
*Attorney, Agent, or Firm*—Millen, White & Zelano

[57] ABSTRACT

An enzymatic reagent, kit and method for determining the concentration of monovalent anions, especially chloride, particularly in clinical samples, and especially in a single-reagent format suitable for automated clinical chemistry analyzers.

21 Claims, 1 Drawing Sheet

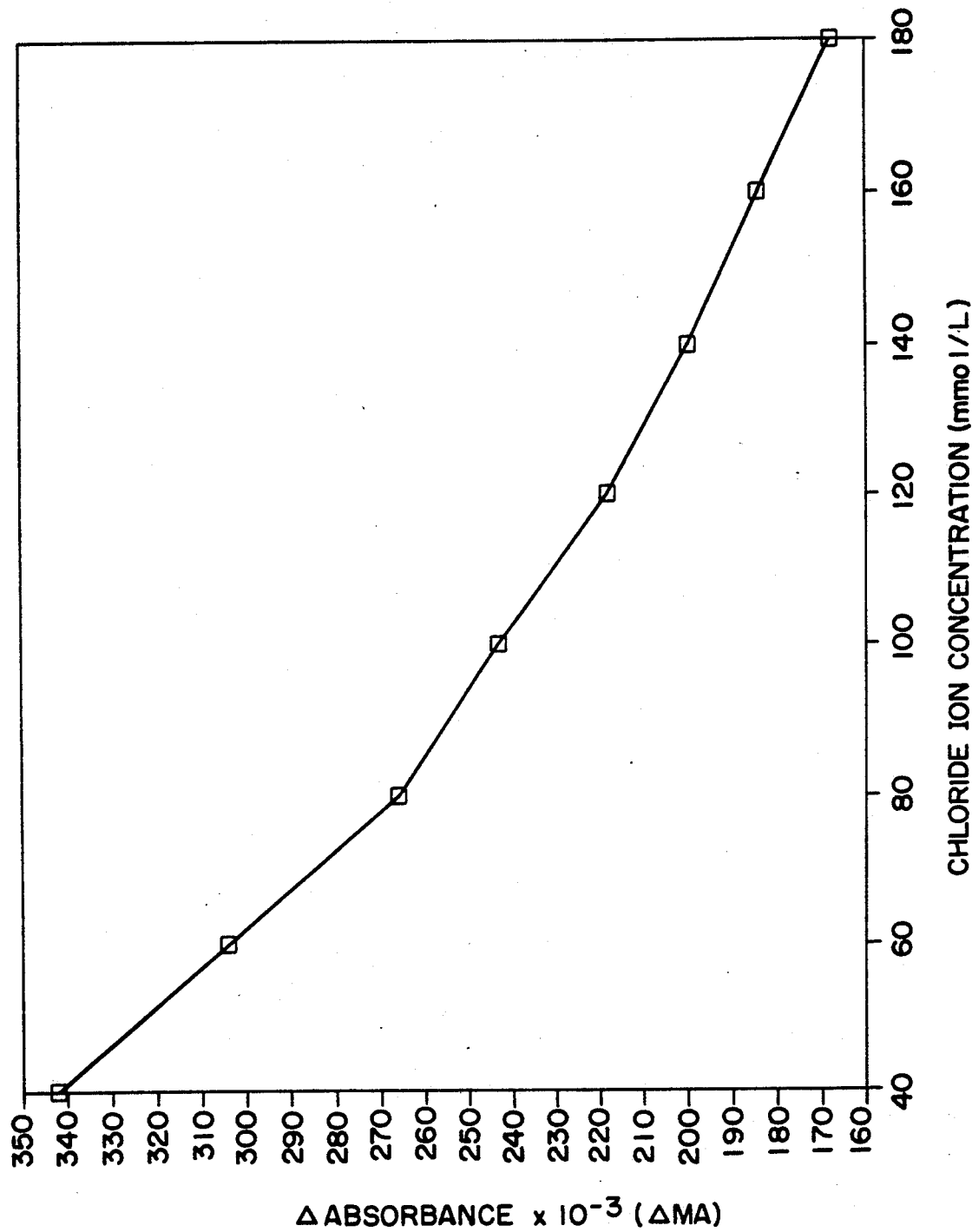

ENZYMATIC DETECTION OF MONOVALENT ANIONS

BACKGROUND OF THE INVENTION

This invention relates to an enzymatic reagent, kit and method for determining the concentration of monovalent anions, especially chloride, particularly in biological fluids, and especially in a single reagent format.

The determination of chloride is routinely made in a wide variety of fluids, e.g., industrial solutions, swimming pools, and in clinical chemistry. The last mentioned is of particular importance because chloride is the major extracellular anion and is therefore significantly involved in the maintenance of water distribution, extracellular electrolyte balance and osmotic pressure. Hypochloremia is observed in Addisonian crisis, certain metabolic acidoses, prolonged vomiting and in metabolic alkalosis. Hyperchloremia is common in dehydration, renal tubular acidosis, acute renal failure, prolonged diarrhea and salicylate intoxication (Tietz, N. W., *Textbook of Clinical Chemistry*, p. 1183, W. B. Saunders Co., Philadelphia, PA, 1986).

Clinically, chloride is commonly measured in urine, serum or plasma, spinal fluid and sometimes in sweat. The most common methods for chloride analysis are mercurimetric titration (Schales, O., and Schales, S. S., J. Biol. Chem., 140, 879–884, 1941.), coulometric titration (Cotlove, E., In: *Methods of Biochemical Analysis*, Vol. 12. D. Glick, Ed. New York, Interscience Publishers, Inc., 1964.), spectrophotometry (Zall, D. M., Fisher, D., and Garner, M. Q., Anal. Chem. 28, 1665–1668, 1956; West, P. W., and Coll, H., Anal. Chem. 28, 1834–1838, 1956; Schoenfeld, R. G., and Lewellen, C. J., Clin. Chem. 10, 533–539, 1964; Hamilton, R. H., Clin. Chem. 12, 1–17, 1966; Law, W. T., and Ertingshausen, G., Clin. Chem. 26, 1874–1877, 1980 [U.S. Pat. No. 4,278,440].), ion selective electrode methodology (Dahms, H., Rock, R., and Seligson, D., Clin. Chem. 14, 859–870, 1968; Rockenmacher, M., Am. J. Clin. Path. 33, 349–354, 1960.) and a recently developed enzymatic assay (Ono, T., Taniguchi, J., Mitsumaki, H., Takahata, F-, Shibuya, A., Kasahara, Y., and Koshimizu, F., Clin. Chem. 34, 552–553, 1988 [U.S. Patent Pending].), but all of these assays suffer from at least one important disadvantage.

Coulometric methods are widely used but time consuming maintenance procedures have reduced their appeal. Ion selective electrodes are becoming the method of choice in most laboratories but they too require extensive maintenance. The mercurimetric titration and most of the spectrophotometric methods contain mercury which creates waste disposal and environmental problems. All of the spectrophotometric methods contain strong acids which necessitate handling precautions and make them unsuitable for tabletting.

The newly developed amylase-based enzymatic assay, as described, is not suitable for unit dose analyzers due to the requirement for a considerable incubation period before the addition of a second reagent for initiating the reaction.

SUMMARY OF THE INVENTION

It is an object of one aspect of this invention to provide an improved test method for measuring monovalent anions, particularly chloride ions, in a sample, particularly of biological origin, which obviate the disadvantages mentioned above.

An object of another aspect of this invention is to provide an improved reagent suitable for chloride ion detection.

An object of still another aspect of the invention is to provide a kit suitable for chloride ion detection.

Upon further study of the specification and appended claims, further objects and advantages of this invention will become apparent to those skilled in the art.

One aspect of these objects has been achieved by providing a reagent for the detection of chloride ions in a sample comprising:

(a) an enzyme which is competitively inhibited by chloride,
(b) a substrate or pseudosubstrate for the enzyme,
(c) optionally one or more cofactors for the enzyme,
(d) optionally a buffering agent, and
(e) optionally an acid, base or salt thereof, effective to provide a pH range suitable for the enzyme, and which does not contain chloride, said reagent being in a dry form or in a liquid form in two or more separate solutions such that at least one of components (a), (b) or (c) is in a different solution prior to use.

Another aspect of these objects has been achieved by providing a method for the detection of chloride ions in a sample comprising the steps of mixing a sample suspected to contain chloride with a reagent comprising:

(a) an enzyme which is competitively inhibited by chloride,
(b) a substrate or pseudosubstrate for the enzyme,
(c) optionally one or more cofactors for the enzyme,
(d) optionally a buffering agent, and
(e) optionally an acid, base or salt thereof, effective to provide a pH range suitable for the enzyme, and which does not contain chloride, said reagent being in a dry form or in a liquid form in two or more separate solutions such that at least one of components (a), (b) or (c) is in a different solution prior to use;

measuring a physical property of the resultant reaction mixture;

measuring said physical property again at a later time; and determining from the two measurements the concentration of chloride in the sample.

Other aspects are achieved in an analogous manner by converting the above-described reagent and method for the determination of the concentration of a different anion.

DETAILED DISCUSSION

It has been discovered that the competitive inhibition by chloride of the enzyme salicylate hydroxylase (E.C.1.14.13.1) can be used as an accurate indicator of chloride concentration in a sample. (The inhibition of the salicylate hydroxylase reaction by chloride is known, per se, in the art of the enzymology of salicylate metabolism (White-Stevens, R. H., and Kamin, H., J. Biol. Chem. 247, 2358–2370, 1972).) It was found that, in the presence of benzoate, m-hydroxybenzoate, or several other substrates or pseudosubstrates, salicylate hydroxylase (SH) will catalyze the conversion of nicotinamide adenine dinucleotide, reduced (NADH) and oxygen to nicotinamide adenine dinucleotide (NAD). Since chloride is a competitive inhibitor of this reaction, as the chloride concentration increases, the rate of NADH conversion to AND decreases. Consumption of NADH is easily measured as a decrease in optical density at the appropriate wavelength.

The test is similar to the amylase-based enzymatic chloride assay in that it contains no strong acids or mercury and therefore presents no difficult handling or disposal problems and also in the fact that it utilizes an enzyme and a kinetic measurement to determine chloride concentration. The present invention, however, relies on the ability of chloride to inhibit rather than activate an enzyme. Furthermore, no additional enzymes are required to produce a signal, much less a time-consuming preincubation step such as is required in the amylase enzyme assay. Since it is a one-step analysis, the invention is readily adaptable to any clinical chemistry analyzer that carries out its own reagent constitution before measurement, such as the E. I. DuPont de Nemours aca ® Analyzer or the Dade Paramax ™ Analyzer. Thus, the present invention presented here does not require mercury or strong acid, is easily tabletted, relatively inexpensive, results in a comparatively accurate assay and is and readily adapted to most clinical chemistry analyzers.

The reaction catalyzed by an enzyme useful in this assay preferably has one or more substrates or pseudosubstrates, co-factors, or products which are detectable by a change in a physical property of the reaction mixture, preferably spectrophotometrically or fluorometrically in a manner and time scale compatible with automated devices used in clinical laboratories. Furthermore, chloride, and/or other monovalent anions, must be a competitive inhibitor of the reaction, such that there is a defined relationship, preferably linear, between monovalent anion concentration and the rate of inhibition in at least a portion of the range of the anion concentration that is expected to be encountered.

The reaction, therefore, will be of the general type:

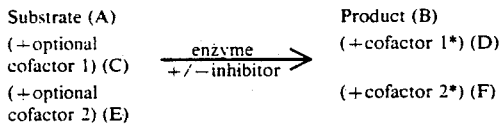

wherein the addition of a monovalent anion inhibitor causes a concentration-dependent decrease in the rate of reaction, and any one of the reactants A-F may be measured, either directly or indirectly, by detecting a physical property; for example, optical density, which can be detected spectrophotometrically or fluorometrically. The sample may be any liquid suspected to contain a monovalent anion which competitively inhibits the enzyme reaction measured at appropriate concentrations of reactants and inhibitor. These are preferably samples of biological origin, most preferably clinical samples. The monovalent anions to be determined may be any which inhibit the reaction, for example, chloride, nitrate, nitrite, bromide, iodide, cyanate and thiocyanate. Detection of chloride is the preferred embodiment of this invention.

Biological samples which may be analyzed for chloride concentration by use of this method include blood, serum, plasma, spinal fluid, urine, sweat, feces, and gastric and intestinal fluids. These samples are prepared for analysis by methods known per se to one skilled in the art for other prior art chloride assay methods. Other types of samples for which this assay may be useful are prepared analogously, i.e., cleared of turbid material by filtration or centrifugation, and concentrated or diluted as necessary to a chloride concentration measurable by the reaction of this invention.

The reagent mixture for the assay of this invention comprises: (a) an enzyme, (b) a substrate, (c) optional cofactors, and usually a buffer, an agent and an acid, base or salt thereof.

The enzyme suitable for this assay is one which is inhibited by the monovalent anion to be tested in a concentration-dependent manner, and which catalyzes a reaction whose inhibition can be measured by a change in a physical property of the reaction mixture, preferably spectrophotometrically or fluorometrically; for example, salicylate hydroxylase or NADH oxidase. Salicylate hydroxylase is preferred for chloride determination.

There are numerous examples in the scientific literature of enzymes which are competitively inhibited to a greater or lesser degree by one or more monovalent anions. The choice of suitable enzyme for use in practicing this invention can be made based on requirements of anion specificity, sensitivity, suitability to available instrumentation, etc., and can be determined by one experienced in the art by routine methods.

The choice of substrate for this reaction depends on the enzyme which is employed. For salrcylate hydroxylase, suitable substrates are of two types; firstly, compounds which can be hydroxylated by the enzyme, which reaction is coupled to the conversion of an electron donor; for example, NADH is oxidized to NAD, or nicotinamide adenine dinucleotide phosphate, reduced (NADPH) can be oxidized to nicotinamide adenine dinucleotide phosphate (NADP), and which reaction is also coupled to the reduction of $O_2$. A second class of compounds which may be employed are of the type known as pseudosubstrates, which bind to the enzyme and allow the oxidation of the electron donor and the reduction of $O_2$, but which themselves are not altered at all, or at least not stoichiometrically (White-Stevens and Kamin, id.). It is notable that in the reaction utilizing pseudosubstrates, $O_2$ is reduced to $H_2O_2$ instead of to $H_2O$. It is preferable that the substrates, pseudosubstrates and reaction products do not interfere in the detection protocol. Examples of suitable substrates or pseudosubstrates for salicylate hydroxylase are meta-hydroxybenzoic acid (m-HBA), para-hydroxybenzoic acid, benzoate, salicylamide, benzamide, and ortho-nitrobenzoate m-HBA is the preferred pseudosubstrate for the detection of chloride ions using salicylate hydroxylase.

Cofactors which may be required for a particular reaction vary with respect to the enzyme, the direction of catalysis by a given enzyme under given reaction conditions, the nature of the reaction being catalyzed, etc. They may be nucleotides which provide chemical energy to drive a thermodynamically unfavorable reaction, for example, adenosine triphosphate (ATP), or conversely, those which store energy from energy-favorable reactions, for example, adenosine monophosphate (AMP) or adenosine diphosphate (ADP). They may be electron donors such as NADH or NADPH, or conversely, electron acceptors such as AND or NADP. They may be flavin-containing electron carriers such as flavin adenine dinucleotide (FAD) or flavin mononucleotide (FMN), in either the oxidized or reduced form. They may be iron-containing electron-transferring proteins, for example, cytochromes. They may be one or more of the oxidized or reduced forms of hydrogen and oxygen, including $H_2$, $H^+$, $OH^-$, $H_2O$, $H_2O_2$, or $O_2$. The cofactors may additionally include a wide variety of other compounds, including proteins, which may change or cause another compound to be changed during the course of the reaction. In addition, there are reactions which do not require cofactors which may also be suitable for the process of this invention.

When salicylate hydroxylase is used as the enzyme for this invention, the cofactor is an electron donor, which may be any one which is suitable for the reaction; for example; NADH or NADPH. NADH is preferred.

Most enzymes have fairly limited pH optima for reactions they catalyze; thus, in most cases, a buffering agent and acid, base, or salt thereof will be required to provide and maintain a specific pH for the final reagent in solution form. The buffering agent can be any of a wide variety of known buffering compounds. For enzymes with pH optima in the range between 6.0 and 10.0, the buffer can be, for example, Tris-(hydroxmethyl-)aminomethane (Tris), N-2-hydroxethyl-piperazine-N'-2-ethane sulfonic acid (HEPES), 1,4-piperazinebis-(ethane sulfonic acid) (PIPES), 2-(N-morpholino)-ethane sulfonic acid (MES), or other amine buffers. For salicylate hydroxylase, Tris buffer is especially preferred. For adjusting the pH, any of a wide variety of known acids, bases or salts thereof, organic or inorganic, may be used. Suitable acids or salts thereof for adjusting the pH of basic buffers are, for example, phosphate, succinate, malate, arsenate, malonate, and cacodylate. Phosphate is especially preferred. Of course, when this assay is used to measure chloride, both the buffer and acid, base or salt thereof must not contain chloride. A similar caveat applies to measurement of other monovalent anions.

Various means may be employed for detection of the rate of inhibition by monovalent anions of the reaction. These include measuring the disappearance of substrate or cofactors, or evolution of products of the reaction. The preferred method for salicylate hydroxylase is by spectrophotometrically monitoring the disappearance of NADH at 340 nm. Other suitable wavelengths may also be monitored; for example, the shoulder of the NADH absorbance peak at approximately 383 nm. In addition, since the reaction using salicylate hydroxylase and pseudosubstrates also generates $H_2O_2$, any of the known means of $H_2O_2$ detection, such as the Trinder systems, can alternatively be used to measure salicylate hydroxylase activity and therefrom chloride or other monovalent anion concentration.

Furthermore, since salicylate hydroxylase is a FAD-containing enzyme, the enzyme can alternatively be coupled to redox dyes, such as, for example, 2,6-dichlorophenolindophenol or methylene blue, for monitoring the reaction. Redox dye coupling methods are well known; for example, see Methods of Enzymatic Analysis, Vol. I, H. U. Bergmeyer, ed., 3rd edition (1983).

The reagent mixture may be formulated in various ways. If used in a liquid format, the invention must be configured as at least a two-reagent system. At least two of the active components, e.g., the substrate and the enzyme, cannot be stored together in a liquid form; one of the components must be stored separately. In the case of salicylate hydroxylase, there are three active components, viz., substrate, enzyme, and elect on donor. one of which must be stored separately. For example, one reagent may contain buffer, substrate, and NADH, while a second reagent contains buffer and enzyme.

The preferred formulation is as a dry powder or tablet. There are numerous acceptable means of manufacturing powders and tablets; they may be prepared by, for example, mixing appropriate amounts of dry acid salt, buffer, optional cofactor(s) and a bulking agent (for example, mannitol or sorbitol) and then granulating this blend with a binder, for example, polyvinylpyrrolidone (PVP). The granules after preferably being sized are sprayed with a mixture of substrate and enzyme in a buffer, and optionally with other conventional additives, e.g., antifoam B. The granules are then preferably coated with a protective lubricant; for example, polyethylene glycol (PEG). The granules may then be tabletted.

Of course, any of a number of alternative -combinations of the reagent compounds may be used as the base of the granules, such that at no time is the enzyme, NADH and substrate or pseudosubstrate present in a liquid form at the same time. Intermediate coatings may be applied to further separate the active ingredients from coming in contact in a liquid form, e.g., during spraying of a solution containing one or more of the active agents upon granules. Many acceptable protocols are known in the art for formulating tablets; the exact nature of the tablet formulation is not critical as long as the following requirements are met:

1) All of the reagents are present in the required quantities in each tablet;
2) The tablet dissolves quickly upon exposure to water;
3) The compounds are stable within the tablet; and
4) None of the stabilizers or coatings interferes with the assay.

It is also possible to perform the assay using immobilized enzyme, for example, on a membrane for use on an enzymatic chloride electrode, or a salicylate electrode, or on a strip of, e.g., filter paper or other solid support as part of an optical solid state assay. In this case, the other elements of the reaction mixture can be kept in a separate dry or liquid format.

The preferred embodiment of this invention is directed to the detection of chloride, but the nature of the inhibition of salicylate hydroxylase by monovalent anions is relatively non-specific. Therefore, this system may also be used to quantitate other monovalent ions, such as, for example, nitrite, nitrate, bromide, iodide, cyanate, thiocyanate, among others. Other suitable enzymes which are inhibited by monovalent anions may exhibit a greater or lesser specificity for one or more of these anions, and may be substituted as requirements of a particular sample to be measured indicate.

Due to the diverse nature of substrates, buffers, acids, bases and salts thereof, enzymes, and sample compositions contemplated by this invention, it is understood by one skilled in this field that variation of the preferred amounts, or substitution of functional equivalents for any of the preferred compounds will result in variations in required concentration, sensitivity and optimal read time for the overall reaction. However, optimization of these parameters for a particular combination of compounds or set of reaction conditions is readily achievable by known routine methods.

The generic and preferred ranges of composition for the preferred compounds of this invention are:

| Component | Generic Range | Preferred Range |
|---|---|---|
| SH | 0.05–20 U/ml | 0.4–3.0 U/ml |
| m-HBA | 0.25–20 mmol/l | 1–5 mmol/l |
| NADH | 0.25–2 mmol/l | 0.3–0.5 mmol/l |
| Tris | 5–650 mmol/l | 150–310 mmol/l |
| KH$_2$PO$_4$ | 5–500 mmol/l | 125–250 mmol/l |

The preferred pH range for this composition is pH 6.0–10.0, most preferably pH 7.5–8.2. The preferred sample to reagent ratio of the final solution is in the range of 1:5 to 1:300.

The tabletted format contains appropriate amounts of each compound to make a solution, upon adding the predetermined amount of water and sample, which corresponds to the ranges listed above.

BRIEF DESCRIPTION OF THE DRAWING

The figure is a graph which summarizes the results of a concentration study which measures the sensitivity of the chloride assay as a function of chloride concentration.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, are hereby incorporated by reference.

EXAMPLES

Example 1: Liquid Format

| Reagent 1: | KH$_2$PO$_4$ | 180 mmol/l |
|---|---|---|
| | Tris | 227 mmol/l |
| | m-Hydroxybenzoic Acid | 2.3 mmol/l |
| | NADH | 0.517 mmol/l |
| | pH 8.0 at 22° C. | |
| Reagent 2: | KH$_2$PO$_4$ | 180 mmol/l |
| | Tris | 227 mmol/l |
| | Salicylate hydroxylase | 16 U/ml |
| | pH 8.0 | |
| Sample size: | 15 ul | |

Sample is added to 435 ul of Reagent 1 that is at 37° C., followed by addition of 50 ul of Reagent 2. Sample is then mixed for a short period of time (3 sec.) and then incubated for 20–40 seconds before the first reading at 340 nm. The second reading is taken from 20–35 seconds after the first. Details of determining concentrations of chloride in a unit dose dry format are given in Example 2.

Example 2: Dry Format

| KH$_2$PO$_4$ | 148.8 g |
|---|---|
| Tris | 167.4 g |
| NADH | 3.0 g |
| Sorbitol | 644.8 g | are mixed and granulated with

| PEG 20,000 | 7.2 g |
|---|---|
| PVP 40,000 | 28.8 g |

The granulation is then sized so that only the 60–80 mesh portion is used in the subsequent coating process. The sized granulation is then sprayed with 200 ml of a coating solution containing a mixture of

| m-Hydroxybenzoic Acid | 1.7 g |
|---|---|
| antifoam B | 18.5 ml |
| salicylate hydroxylase | 12,363 U |
| Bovine serum albumin | 2.0 g |
| NaH$_2$PO$_4$ | 0.17 g |
| Distilled water | 200 ml | at pH 8.0. The granules are dried, and then coated with about 7.2 mg/g of PEG 20,000 and 28.8 mg/g of PVP 40,000. The final product is sized once more and only the 40–80 mesh portion is used for tabletting.

The ratio of sample to the total amount of water used to reconstitute the tablet (or powder) is 1:31. After the sample is added along with the water, the mixture is vortexed in the reaction cuvette for ten seconds. Following a 15-second incubation, an absorbance reading at 340 nm is taken, followed by a second reading 25 seconds later. The entire process takes place at 37° C. The change in absorbance when plotted versus the chloride concentration in the sample gives a decreasing hyperbolic standard curve over a 40 to 180 mmol/L sample chloride concentration range. (See FIG. 1.) Over the 80 to 120 mmol/L range, the curve is very nearly linear and gives a sensitivity that is almost 2 mA/mmol/L chloride. The total analysis time from sample addition to the final reading is less than a minute.

Example 3: Performance Characteristics

Various parameters of performance required for the reagent were studied. These results are summarized in Table 1.

TABLE 1

| PARAMETERS | |
|---|---|
| 1. ASSAY RANGE | 80–120 mmol/L CHLORIDE |
| 2. PRECISION (UNIT DOSE FORMAT) | 1.02%–1.55% |
| 3. ACCURACY (% RECOVERY) | 95–105% |
| 4. CORRELATION WITH AN ION SELECTIVE ELECTRODE METHOD | SLOPE = 0.977 INTERCEPT = 3.4 |
| 5. INTERFERENCES | |
| TRIGLYCERIDES | NONE UP TO 1000 mg/dL |
| BILIRUBIN | NONE UP TO 20 mg/dL |
| HEMOGLOBIN | POSITIVE INTERFERENCE AT >100 mg/dL |
| SALICYLATE | POSITIVE INTERFERENCE AT >20 mg/dL |
| BROMIDE | POSITIVE INTERFERENCE AT >12 mg/dL |
| FLUORIDE | NONE |
| ASCORBATE | NONE |
| OXALATE | NONE |
| CAFFEINE | NONE |
| ACETAMINOPHEN | NEGATIVE INTERFERENCE AT >20 mg/dL |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for the detection of chloride ions in a sample comprising the steps of:
   mixing a sample suspected to contain chloride with a reagent comprising
   (a) an enzyme which is competitively inhibited by chloride,
   (b) a substrate or pseudosubstrate for the enzyme, and optionally
   (c) at least one cofactor for the enzyme; measuring an optical property of the resultant reaction mixture;
   measuring said optical property again at a later time; and
   determining from the measurements the concentration of chloride in the sample.

2. A method of claim 1, wherein the reagent further comprises:
   (d) a buffering agent and optionally
   (e) an acid, base or salt thereof, effective to provide a pH range suitable for the enzyme, and which does not contain chloride.

3. A method of claim 2, wherein the enzyme is salicylate hydroxylase.

4. A method of claim 3, wherein the cofactor is an electron donor.

5. A method of claim 4, wherein the cofactor is NADH.

6. A method of claim 4, wherein the cofactor is NADPH.

7. A method of claim 5, wherein the component (d) is meta-hydroxbenzoic acid, salicylate, para-hydroxybenzoate, benzoate, salicylamide, benzamide, or ortho-nitrobenzoate.

8. A method of claim 7, wherein-the component (d) is meta-hydroxybenzoic acid.

9. A method of claim 8, wherein the buffering agent is Tris(Tris[hydroxymethyl]aminomethane).

10. A method of claim 9, wherein component (e) is $KH_2PO_4$.

11. A method of claim 10, wherein the reagent comprises
    (a) 0.05–20 U/ml salicylate hydroxylase,
    (b) 0.25–20 mmol/l meta-hydroxybenzoic acid,
    (c) 0.25–2 mmol/l NADH
    (d) 5–650 mmol/l Tris, and
    (e) 5–500 mmol/l $KH_2PO_4$ at pH 6.0–10.0.

12. A method of claim 2, wherein components (a), (b), (c), (d) and (e) are in a dry form.

13. A method of claim 12, wherein components (a), (b), (c), (d) and (e) are in the form of a tablet.

14. A method of claim 2, wherein components (a), (b), (c), (d) and (e) are in a liquid form and are in two or more separate solutions such that at least one of components (a), (b), or (c) is in a different solution prior to use.

15. A method of claim 2, wherein the sample is a biological material chosen from the group consisting of blood, serum, plasma, spinal fluid, urine, sweat, feces, gastric fluid and intestinal fluid.

16. A method of claim 11, wherein the optical property measured is optical density.

17. A method of claim 16, wherein the optical is measured at 340 nm.

18. A method of claim 16, wherein the optical density is measured at a wavelength suitable for detecting $H_2O_2$ evolution.

19. A method of claim 11, wherein the enzyme is coupled to a redox dye.

20. A method of claim 19, wherein the physical property measured is optical density.

21. A method of claim 2, wherein the enzyme is immobilized on a solid support.

* * * * *